United States Patent
Heerding et al.

(10) Patent No.: US 6,559,172 B1
(45) Date of Patent: May 6, 2003

(54) DISUBSTITUTED IMIDAZOLES USEFUL IN THE TREATMENT OF BACTERIAL INFECTIONS

(75) Inventors: Dirk Heerding, Malvern, PA (US); Kenneth A. Newlander, West Chester, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/979,560

(22) PCT Filed: May 24, 2000

(86) PCT No.: PCT/US00/14330

§ 371 (c)(1), (2), (4) Date: Nov. 14, 2001

(87) PCT Pub. No.: WO00/71120

PCT Pub. Date: Nov. 30, 2000

Related U.S. Application Data

(60) Provisional application No. 60/135,948, filed on May 25, 1999.

(51) Int. Cl.$^7$ ............... A61K 31/4164; A61K 31/4174; C07D 233/56; C07D 405/06; C07D 409/06
(52) U.S. Cl. .................... 514/396; 514/397; 548/311.7; 548/315.1; 548/343.5; 548/346.1; 548/335.1
(58) Field of Search ............... 548/311.7, 315.1, 548/343.5, 346.1, 335.1; 514/396, 397

(56) References Cited

U.S. PATENT DOCUMENTS

| | | |
|---|---|---|
| 3,657,441 A | 4/1972 | Jensen et al. ............... 424/273 |
| 4,218,458 A | 8/1980 | Heeres et al. |
| 5,179,210 A | 1/1993 | Ebel ......................... 548/335.1 |
| 5,620,944 A * | 4/1997 | Nakanishi et al. .......... 504/275 |

FOREIGN PATENT DOCUMENTS

| | | |
|---|---|---|
| FR | 2482859 | * 11/1981 |
| WO | WO 99/01128 | 1/1999 |

OTHER PUBLICATIONS

Kempter et al., CA 70:11630, 1969.*
Baldwin et al., CA 105:24227, 1986.*
Baldwin, et al., J. Med. Chem., 1986, vol. 29, No. 6, pp. 1065–1080.
Suzuki, et al., Chem. & Pharma Bulletin, 1986, vol. 34, No. 8, pp. 3111–3120.
Poretta, et al., Farmaco, 1991, vol. 46, No. (7,8), pp. 913–924.
Poretta, et al., Farmco—Ed. Sci., 1985, vol. 40, No. 6, pp. 404–416.
Iradyan, et al., Chem. Abstracts, 1974, vol. 81, No. 15, Abstract No. XP–002199705 (91428g).
Baggaley, et al., J. Med. Chem., 1975, vol. 18, No. 8, pp. 833–836.
Tsuge, et al., Heterocycles, 1975, vol. 3, No. 7, pp. 547–552.
Iradyan, et al., Chem. Abstrcts, 1985, vol. 102, No. 1, abstract No. XP–002199706. (6304y).

* cited by examiner

Primary Examiner—Laura L. Stockton
(74) Attorney, Agent, or Firm—Laura K. Madden; Mary E. McCarthy; Charles M. Kinzig

(57) ABSTRACT

Novel disubstituted imidazoles are disclosed which are useful in the treatment of bacterial infections, particularly through the inhibition of FAB I.

1 Claim, No Drawings

DISUBSTITUTED IMIDAZOLES USEFUL IN THE TREATMENT OF BACTERIAL INFECTIONS

This is a 371 of International Application PCT/US00/14330, filed May 24, 2000, which claims benefit from the following U.S. Provisional Application No.: 60/135,948 filed May 25, 1999.

FIELD OF THE INVENTION

This invention relates to pharmaceutically active compounds which are useful for the treatment of bacterial infections.

BACKGROUND OF THE INVENTION

There is a medical need for novel antibiotics and a market opportunity for new antibacterial agents. Thus, the object of this invention is to identify novel compounds having antibiotic activity.

While the overall pathway of saturated fatty acid biosynthesis is similar in all organisms, the fatty acid synthase (FAS) systems vary considerably with respect to their structural organization. Vertebrates and yeast possess a FAS in which all the enzymatic activities are encoded on one or two polypeptide chains, respectively, and the acyl carrier protein (ACP) is an integral part of the complex. In contrast, in bacterial FAS, each of the reactions is catalyzed by a distinct, mono-functional enzyme and the ACP is a discrete protein. Therefore, there is considerable potential for the selective inhibition of the bacterial system by antibacterial agents.

Fab I (previously designated EnvM) functions as an enoyl-ACP reductase (Bergler, et al, (1994), *J. Biol. Chem.* 269, 5493–5496) in the final step of the four reactions involved in each cycle of bacterial fatty acid biosynthesis. In this pathway, the first step is catalyzed by β-ketoacyl-ACP synthase, which condenses malonyl-ACP with acetyl-CoA (FabH, synthase III). In subsequent rounds, malonyl-ACP is condensed with the growing-chain acyl-ACP (FabB and FabF, synthases I and II, respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP, which in turn is converted to acyl-ACP by NADH-dependent enoyl-ACP reductase (Fab I). Further rounds of this cycle, adding two carbon atoms per cycle, eventually lead to palmitoyl-ACP (16C), where upon the cycle is stopped largely due to feedback inhibition of Fab I by palmitoyl-ACP (Heath, et al, (1996), *J. Biol. Chem.* 271, 1833–1836). Thus, Fab I is a major biosynthetic enzyme and is a key regulatory point in the overall synthetic pathway of bacterial fatty acid biosynthesis. Therefore, Fab I is an ideal target for antibacterial intervention.

Studies have shown that diazaborine antibiotics inhibit fatty acid, phospholipid and, lipopolysaccharide (LPS) biosynthesis and that the antibacterial target of these compounds is Fab I. For example, derivative 2b18 from Grassberger, et al (1984) *J. Med Chem* 27 947–953 has been reported to be a non-competitive inhibitor of Fab I (Bergler, et al, (1994), *J. Biol. Chem.* 269, 5493–5496). Also, plasmids containing the Fab I gene from diaborine resistant *S. typhimurium* conferred diazaborine resistance in *E. coli* (Turnowsky, et al, (1989), *J. Bacteriol.*, 171, 6555–6565). Furthermore, inhibition of Fab I either by diazaborine or by raising the temperature in a Fab I temperature sensitive mutant is lethal. These results demonstrate that Fab I is essential to the survival of the organism (Bergler, et al, (1994), *J. Biol. Chem.* 269, 5493–5496).

Recent studies have shown that Fab I is also the target for the broad spectrum antibacterial agent triclosan (McMurry, et al, (1998) *Nature* 394, 531–532). A crystal structure of the *E. coli* Fab I complexed with NAD and triclosan shows that triclosan acts as a site-directed, very potent inhibitor of Fab I by mimicking its natural substrate (Levy, et al, (1999) *Nature* 398, 383–384). Ward, et al ((1999) *Biochem.* 38, 1251412525) have shown that there is no evidence for the formation of a covalent complex between Fab I and triclosan, which would be analogous to the diazaborines; triclosan differs from these compounds in that it is a reversible inhibitor of Fab I. The structural data for the complex of Fab I with NAD and triclosan provides important information about Fab I as a therapeutic target.

Importantly, it has now been discovered that certain compounds have antibacterial activity and some of these antibacterial compounds are Fab I inhibitors. Therefore, the compounds of the present invention may be useful for the treatment of bacterial infections in mammals, particularly in man.

SUMMARY OF THE INVENTION

This invention comprises compounds of formula (I) and formula (II), as described hereinafter, which are useful in the treatment of bacterial infections.

This invention is also a pharmaceutical composition comprising a compound according to formula (I) or formula (II) and a pharmaceutically acceptable carrier.

This invention is also a method of treating bacterial infections by inhibiting Fab I. In a particular aspect, the compounds of this invention are useful as antibacterial agents.

DETAILED DESCRIPTION

This invention comprises compounds of formula (I) or formula (II):

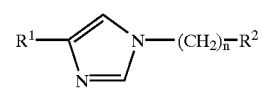

or

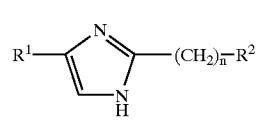

wherein:

$R^1$ is $C_{1-4}$alkyl, Ar or 2-thienyl or 3-thienyl;
$R^2$ is $C_{1-4}$alkyl or Ar; and
n is 0–3;
or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique racemic compound, as well as each unique nonracemic compound. These compounds may be synthesized and resolved by conventional techniques.

In cases in which compounds have unsaturated carbon-carbon double bonds, both the cis (Z) and trans (E) isomers are within the scope of this invention. In cases wherein compounds may exist in tautomeric forms, such as keto-enol tautomers, such as

and

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) or in formula (II) in vivo.

The compounds of formula (I) and formula (II) may be useful in the treatment of bacterial infections. Also, the compounds of this invention may be useful as antifungal agents. Additionally, the compounds may be useful in combination with known antibiotics.

Preferably, the compounds of the invention comprise compounds of the formula (I):

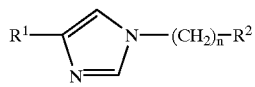

(I)

wherein:
R$^1$ is C$_{1-4}$alkyl, Ar or 2-thienyl or 3-thienyl;
R$^2$ is C$_{1-4}$alkyl or Ar; and
n is 0–3;
or a pharmaceutically acceptable salt thereof.

With respect to formula (I):
Suitably, R$^2$ is Ar. Preferably, R$^2$ is phenyl, unsubstituted or substituted by one or two substituents selected from the group consisting of C$_{1-4}$alkyl, C$_{1-4}$alkoxy, CF$_3$, F, Cl, Br and I, or methylenedioxy. Preferably, n is 1.

Suitably, R$^1$ is Ar or Het. Preferably, R$^1$ is 2- or 3-thienyl or phenyl, unsubstituted or substituted by one or two substituents selected from the group consisting of C$_{1-4}$alkyl, C$_{1-4}$alkoxy, CF$_3$, F, Cl, Br and I.

Alternately, the compounds of the invention comprise compounds of the formula (II):

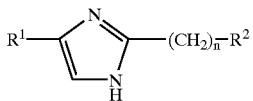

(II)

wherein:
R$^1$ is C$_{1-4}$alkyl, Ar or 2-thienyl or 3-thienyl;
R$^2$ is C$_{1-4}$alkyl or Ar; and
n is 0–3;
or a pharmaceutically acceptable salt thereof.

With respect to formula (II):
Suitably, R$^2$ is Ar. Preferably, R$^2$ is phenyl, unsubstituted or substituted by one or two substituents selected from the group consisting of C$_{1-4}$alkyl, C$_{1-4}$alkoxy, CF$_3$, F, Cl, Br, I and phenyl, or methylenedioxy. Preferably, n is 1.

Suitably, R$^1$ is Ar. Preferably, R$^1$ is phenyl or naphthyl, unsubstituted or substituted by one or two substituents selected from the group consisting of C$_{1-4}$alkyl, C$_{1-4}$alkoxy, CF$_3$, F, Cl, Br, I and phenyl.

Representative of the novel compounds of this invention are the compounds named in Examples 1–91.

Representative of the antibacterial compounds having Fab I inhibitory activity are the following:
1-Benzyl-4-(2-thienyl)-1H-imidazole;
1-Benzyl-4-(3-thienyl)-1H-imidazole;
1-Benzyl-4-(4-methoxyphenyl)-1H-imidazole:
1-(4-Methylbenzyl)-4-(3-thienyl)-1H-imidazole;
4-(4-Methoxyphenyl)-1-(4-methylbenzyl)-1H-imidazole;
1-(4-Chlorobenzyl)-4-(2-thienyl)-1H-imidazole;
1-(4-Chlorobenzyl)-4-(3-thienyl)-1H-imidazole;
1-(4-Chlorobenzyl)-4-(4-methoxyphenyl)-1H-imidazole;
1-(3,4-Dichlorobenzyl)-4-(2-thienyl)-1H-imidazole;
1-(3,4-Dichlorobenzyl)-4-[4-(trifluoromethyl)phenyl]-1H-imidazole;
1-(3,4-Dichlorobenzyl)-4-phenyl-1H-imidazole;
1-(4-Methoxybenzyl)-4-(3-thienyl)-1H-imidazole;
1-(4-Methoxybenzyl)-4-(4-methoxyphenyl)-1H-imidazole;
1-Benzo[1,3]dioxol-5-ylmethyl-4-thiophen-3-yl-1H-imidazole;
4-(2-Methoxy-phenyl)-1-naphthalen-2-ylmethyl-1H-imidazole;
1-(2,4-Dichloro-benzyl)-4-thiophen-3-yl-1H-imidazole;
4-Thiophen-3-yl-1-(3-m-tolyl-propyl)-1H-imidazole;
1-[3-(4-Methoxy-phenyl)-propyl]4-thiophen-3-yl-1H-imidazole;
4-Thiophen-3-yl-1-[3-(3-trifluoromethyl-phenyl)-propyl]-1H-imidazole;
1-(4-Isopropyl-benzyl)-4-thiophen-3-yl-1H-imidazole;
1-[3-(3-Methoxy-phenyl)-propyl]-4-thiophen-3-yl-1H-imidazole;
1-(4-Ethyl-benzyl)-4-thiophen-3-yl-1H-imidazole;
1-(4-Methylbenzyl)-4-phenyl-1H-imidazole; or
1-(4-Methylbenzyl)-4-(2-thienyl)-1H-imidazole;
or a pharmaceutically acceptable salt thereof.

Abbreviations and symbols commonly used in the peptide and chemical arts are used herein to describe the compounds of this invention.

C$_{1-4}$alkyl as applied herein means an optionally substituted alkyl group of 1 to 4 carbon atoms, and includes methyl, ethyl, n-propyl, isopropyl, n-butyl, isobutyl and t-butyl. Any C$_{1-4}$alkyl may be optionally substituted with the group R$^x$, which may be on any carbon atom that results in a stable structure and is available by conventional synthetic techniques. Suitable groups for R$^x$ are C$_{1-4}$alkyl, C$_{1-4}$alkoxy, CF$_3$, F, Cl, Br, I or N(R)$_2$, in which each R' independently is H, C$_1$–C$_4$alkyl or Ar-C$_{0-6}$alkyl.

C$_{1-4}$alkoxy as applied herein means an alkyl group of 1 to 4 carbon atoms attached to an oxygen atom. C$_{1-4}$alkoxy includes methoxy, ethoxy, propoxy and butyloxy.

Halogen or halo means F, Cl, Br, and I.

Ar, or aryl, as applied herein, means phenyl or naphthyl, or phenyl or naphthyl substituted by one to three substituents, such as $C_{1-4}$alkyl, $C_{1-4}$alkoxy, $CF_3$, F, Cl, Br, I or phenyl, or methylenedioxy, that are available by chemical synthesis and are stable are within the scope of this invention.

Certain radical groups are abbreviated herein. t-Bu refers to the tertiary butyl radical, Ph refers to the phenyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl.

The compounds of formula (I) are generally prepared by the following processes:

(i) heating a compound of formula (III) with a compound of formula (IV):

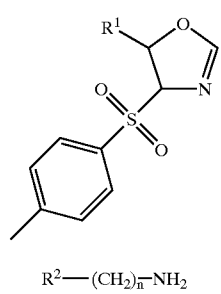

(III)

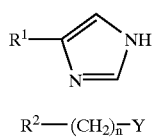

(IV)

wherein $R^1$, $R^2$ and n are as defined in formula (I), with any reactive functional groups protected; or (ii) reacting a compound of formula (IV) with a compound of formula (V):

(IV)

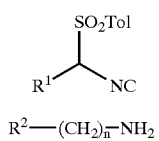

(V)

wherein $R^1$, $R^2$ and n are as defined in formula (I) and Y is halo, methanesulfonyl, toluenesulfonyl, or trifluoromethanesulfonate, with any reactive functional groups protected, in the presence of a base in an aprotic solvent; or (ii) reacting a compound of formula (VI) with a compound of formula (VII):

(VI)

(VII)

wherein $R^1$, $R^2$ and n are as defined in formula (I), with any reactive functional groups protected, in the presence of glyoxylic acid and a base;

and thereafter removing any protecting groups, and optionally forming a pharmaceutically acceptable salt.

The compounds of formula (II) are generally prepared by reacting a compound of formula (VIII) with a compound of formula (IX):

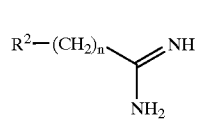

(VIII)

(IX)

wherein $R^1$, $R^2$ and n are as defined in formula (II), with any reactive functional groups protected;

and thereafter removing any protecting groups, and optionally forming a pharmaceutically acceptable salt.

Compounds of the formula (I) are prepared by the general methods described in Scheme 1.

Scheme 1

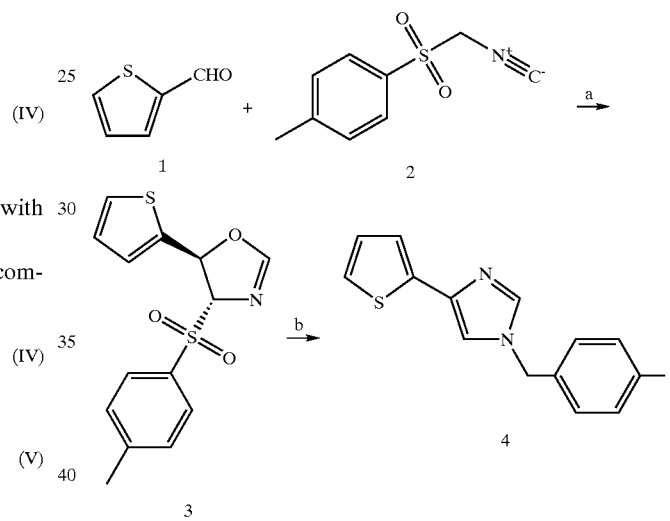

(a) NaCN (10 mol %), EtOH; (b) 4-methylbenzylamine, toluene, 105° C.

Compounds of formula (I) are prepared by methods analogous to those shown in Scheme 1. Alkyl or aryl aldehydes, such as the 1-Scheme 1 compound, are condensed with tosylmethylisocyanide in a dipolar cycloaddition catalyzed by sodium cyanide to give oxazolines, such as the 3-Scheme 1 compound. The oxazolines, for example the 3-Scheme 1 compound, are then heated with primary amines, such as 4-methylbenzylamine, to give the imidazoles of formula (I), such as the 4-Scheme 1 compound.

Alternatively, compounds of formula (I) are generally prepared as described in Scheme 2.

Scheme 2

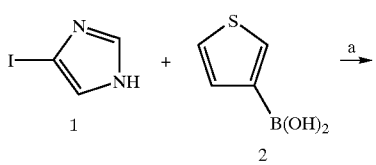

-continued

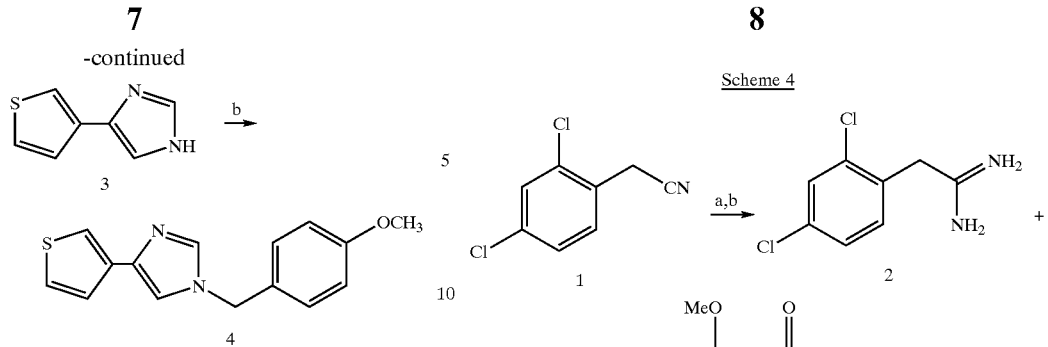

(a) Pd(Ph$_3$P)$_4$, Na$_2$CO$_3$, DME/H$_2$O, reflux; (b) 4-methoxybenzyl bromide, K$_2$CO$_3$, DMF, 80° C.

Compounds of formula (I) are prepared by methods analogous to those shown in Scheme 2. 4-Iodo-1H-imidazole, prepared according to Cliff and Pyne (*Synthesis*, 1994, 681–682) is condensed with a suitable organo-boronic acid, such as 2-Scheme 2, under Suzuki coupling conditions to give the corresponding substituted imidazole. 3-Scheme 2. Typical Suzuki conditions use a catalytic amount of a Pd(0) catalysts, such as tetrakistriphenylphosphine palladium, and an excess of a base, such as sodium carbonate, in a polar solvent, such as dimethoxyethane and water. The substituted imidazole is then alkylated with an alkyl halide, such as 4-methoxybenzyl bromide, in the presence of a base, such as potassium carbonate, in a polar aprotic solvent, such as DMF to give an imidazole of formula (I), such as 4-Scheme 2. Other suitable alkylating agents include alkyl mesylates, alkyl tosylates and alkyl triflates.

Alternatively, compounds of formula (I) are generally prepared as described in Scheme 3.

Scheme 3

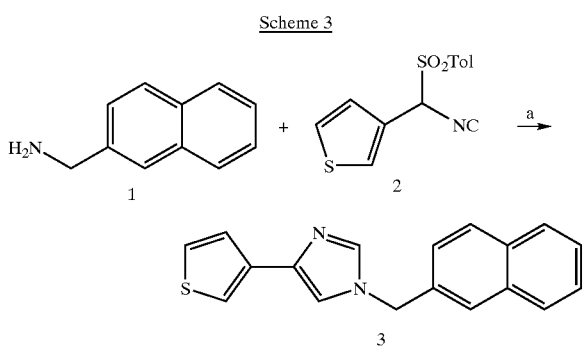

(a) glyoxylic acid, K$_2$CO$_3$, DMF.

Compounds of formula (I) are prepared by methods analogous to those shown in Scheme 3. A primary amine, such as 1-Scheme 3, is condensed with an aryl substituted tosyl methyl isocyanates, such as 2-Scheme 3, in the presence of glyoxylic acid and a base, such as K$_2$CO$_3$, to give a compound of formula (I), such as 3-Scheme 3. The substituted tosyl methyl isocyanate. 2-Scheme 3, is prepared according to Sisko, Mellinger, Sheldrake and Baine (*Tetrahedron Letters*, 1996, 37(45), 8113–8116).

Compounds of the formula (II) are prepared by the general methods described in Scheme 4.

(a) HCl, EtOH; (b) NH$_3$, EtOH: (c) CHCl$_3$, room temperature

Compounds of formula (II) are prepared by methods analogous to those shown in Scheme 4. Aryl or alkyl nitriles, such as the 1-Scheme 4 compound, are converted to the corresponding amidine, such as the 2-Scheme 4 compound, via the corresponding imidate. The amidines are condensed with suitable alpha halo ketones, such as the 3-Scheme 4 compound, to give compounds of formula (II), such as the 4-Scheme 4 compound.

The formula (I) and formula (II) compounds of the present invention may also be prepared by methods known to those skilled in the art. For example, compounds of formula (I) may be synthesized according to the method of Horne, D. A.; Yakushijin, K.; Büchi, G. *Heterocycles*, 1994, 39, 139–153 and compounds of formula (II) may be synthesized according to the method of Caroon. J. M.; Clark, R. D.; Kluge, A. F.; Olah, R.; Repke, D. B.; Unger, S. H.; Michel, A. D.; Whiting, R. L. *J. Med. Chem.*, 1982, 25(6), 666–670. Reference should be made to said articles for their full disclosure, particularly to the methods of preparing the compounds described therein, said disclosures being incorporated herein by reference.

Acid addition salts of the compounds of the invention are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li$^+$, Na$^+$, K$^+$, Ca$^{++}$, Mg$^{++}$ and NH$_4^+$ are specific examples of cations present in pharmaceutically acceptable salts.

This invention also provides a pharmaceutical composition which comprises a compound according to formula (I) or formula (II) and a pharmaceutically acceptable carrier. Accordingly, the compounds of formula (I) and formula (II)

may be used in the manufacture of a medicament. Pharmaceutical compositions of the compounds of formula (I) and formula (II) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients, such as cocoa butter, glycerin, gelatin or polyethylene glycols, and molded into a suppository.

For topical administration, the compounds of this invention may be combined with diluents to take the form of ointments, gels, pastes, creams, powders or sprays. The compositions which are ointments, gels, pastes or creams contain diluents, for example, animal and vegetable fats, waxes, paraffins, starch, tragacanth, cellulose derivatives, polyethylene glycols, silicones, bentonites, silicic acid, talc and zinc oxide, or mixtures of these substances. The compositions which are powders or sprays contain diluents, for example, lactose, talc, silicic acid, aluminum hydroxide, calcium silicate and polyamide powder, or mixtures of these substances. Additionally, for topical ophthalmologic administration, the typical carriers are water, mixtures of water and water miscible solvents, such as lower alkanols or vegetable oils, and water-soluble non-toxic polymers, for example cellulose derivatives, such as methyl cellulose.

The compounds described herein are useful for treating bacterial infections. Also, certain compounds of this invention are Fab I inhibitors. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Also, the compounds of this invention may be useful as antifungal agents.

The compounds of this invention are administered to the patient, in a manner such that the concentration of drug is sufficient to treat bacterial infections. The pharmaceutical composition containing the compound is administered at an oral dose of between about 10 mg to about 1000 mg, taken once or several times daily, in a manner consistent with the condition of the patient. Preferably, the oral dose would be about 50 mg to about 500 mg, although the dose may be varied depending upon the age, body weight and symptoms of the patient. For acute therapy, parenteral administration is preferred. An intravenous infusion of the compound of formula (I) in 5% dextrose in water or normal saline, or a similar formulation with suitable excipients, is most effective, although an intramuscular bolus injection is also useful. The precise level and method by which the compounds are administered is readily determined by one skilled in the art.

The compounds may be tested in one of several biological assays to determine the concentration of compound which is required to have a given pharmacological effect.

Cloning of S. aureus FabI

The fabI gene was cloned from the chromosomal DNA of S. aureus strain WCUH29 using the polymerase chain reaction. Amplification was performed using Taq DNA polymerase (BRL) and the following primers:

5'-CGC CTCGAGATGTTAAATCTGAAAACAAAACATAT-GTC-3' and 5'-CGCGGATCCAATCAAGTCAGGTT-GAAATATCCA-3' (XhoI and BamHI sites underlined). The resulting fragment was then digested with XhoI and BamHI and ligated into XhoI- and BamHI-digested expression vector pET-16b (Novagen), producing pET-His$_{10}$fabI. The gene sequence of fabI was confirmed by automated cycle sequencing using an Applied Biosystems model 377 machine. The untagged version of pET-fabI was constructed by digesting pET-His$_{10}$-fabI with NcoI and NdeI to remove a 97 bp fragment encoding the His 10 tag, the factor Xa cleavage site and the first 8 amino acids of FabI, and replacing it with a linker encoding the first 8 amino acids of FabI plus a glycine residue between the initiator methionine and the lysine at position 2. This plasmid was called pET-fabI. The linker was made by annealing the following two oligonucleotides:

5'-CATGGGCTTAAATCTTGAAAACAAAACA-3' and 5'TATGTTTTGTTTTCAAGATTTAAGCC-3'. The linker sequence in pET-fabI was confirmed by dideoxy sequencing. Only native FabI was used for compound evaluation. For overproduction of native FabI, plasmid pET-fabI was transformed into BL21(DE3) (Novagen) cells, to form strain BL21(DE3):pET-fabI.

Purification of S. aureus FabI

S. aureus FabI was expressed as soluble protein to 10% of total cell protein, 400 g cells being recovered from 15 L fermentation in tryptone phosphate medium. The cells were lysed and the sample centrifuged. The resulting supernatant was filtered and purified using three consecutive chromatography columns: ion-exchange (Sourse 15Q), dye-affinity (Blue sepharose), and size exclusion chromatography columns (Superose 12). After each column the FabI containing fractions were pooled, concentrated, and checked for purity and biological activity.

Cloning of E. coli FabI

A PCR fragment of correct size for E. coli FabI was PCR amplified from E. coli chromosomal DNA, subcloned into the TOPO TA cloning vector, and verified by colony PCR+ restriction endonuclease analysis. The presumptive E. coli FabI PCR fragment was subcloned into the expression vector pBluePet. The FabI clone was transformed into E. coli strain BL21(DE3). Small Scale expression studies show an over-expressed protein band of correct molecular weight (~28 Kda) for E. coli FabI clearly visible following Coomassie staining of SDS PAGE gels. DNA sequencing of the E. coli FabI expression constructs illustrated that no errors were apparent. N' terminal amino acid sequencing has confirmed the over-expressed protein band to be E. coli FabI.

Purification of E. coli FabI

E. coli FabI was expressed as soluble protein to 15% of total cell protein, 120 g cells being recovered from 3 L fermentation in shake flasks in modified terrific broth. The cells were lysed and the sample centrifuged. The resulting supernatant was filtered and purified using three consecutive chromatography columns: ion-exchange (Sourse 15Q), dye-affinity (blue sepharose), and size exclusion (superose 12). After each column the FabI containing fractions were pooled, concentrated and checked for purity and biological activity.

S. aureus FabI Enzyme Inhibition Assay

Assays were carried out in half-area, 96-well microtitre plates. Compounds were evaluated in 50-uL assay mixtures containing 100 mM NaADA, pH 6.5 (ADA=N-[2-acetamido]-2-iminodiacetic acid), 4% glycerol. 0.25 mM crotonoyl CoA, 1 mM NADH, and an appropriate dilution of S. aureus FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control.

E. coli FabI Enzyme Inhibition Assay

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of E. coli FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compound was tested in serial two-fold dilutions ranging from 0.06 to 64 mg/mL. A panel of 12 strains were evaluated in the assay. This panel consisted of the following laboratory strains: Staphylococcus aureus Oxford, Staphylococcus aureus WCUH29, Streptococcus pneumoniae 1629, Streptococcus pneumoniae N1387, Streptococcus pneumoniae ERY2, Enterococcus faecalis I, Enterococcus faecalis 7, Haemophilus influenzae Q1, Haemoplilus influenzae NEMC1, E. coli 7623 (AcrAB$^+$), E. coli 120 (AcrAB$^-$),- and-Morexalla catarrhalis 1502. The minimum inhibitory concentration (MIC) was determined as the lowest concentration of compound that inhibited visible growth. A mirror reader was used to assist in determining the MIC endpoint.

One skilled in the art would consider any compound with a MIC of less than 256 µg/mL to be a potential lead compound. Preferably, the compounds used in the antimicrobial assays of the present invention have a MIC value of less than 128 µg/mL. Most preferably, said compounds have a MIC value of less than 64 µg/mL.

The examples which follow are intended in no way to limit the scope of this invention, but are provided to illustrate how to make and use the compounds of this invention. Many other embodiments will be readily apparent to those skilled in the art.

EXAMPLES

General

Proton nuclear magnetic resonance ($^1$H NMR) spectra were obtained at 300 MHz and chemical shifts are reported in parts per million (δ) downfield from the internal standard tetramethylsilane. Mass spectra were obtained using electrospray (ES) ionization techniques. Elemental analyses were performed by Quantitative Technologies Inc., Whitehouse, N.J. E. Merck Silica Gel 60 F-254 thin layer plates were used for thin layer chromatography. Flash chromatography was carried out on E. Merck Kieselgel 60 (230–400 mesh) silica gel. Reverse phase flash chromatography was carried out on YMC-Gel (S20-120A) reverse phase silica gel. Radial chromatography was carried out on a Chromatotron (Model 8924; Harrison Research Company, Palo Alto, Calif.). Preparative HPLC was performed using Gilson chromatography systems.

All other materials and solvents were obtained from commercial sources and were used without further purification.

Preparation 1

Preparation of (4R*,5S*)-5-(2-Thienyl)-4-toluenesulfonyl-4,5-dihydro-1,3-oxazole A mixture of tosylmethylisocyanide (0.75 g, 3.84 mmol), 2-thiophenecarboxaldehyde (0.37 mL, 3.96 mmol) and sodium cyanide (0.02 g, 0.40 mmol) in EtOH (10 mL) was stirred at room temperature for 2 h. The solvent was removed to give the desired compound as a tan solid. This material was used without further purification. MS(ES+) m/z 614.8 (2M+H$^+$).

Preparation 2

Preparation of (4R*,5S*)-5-(3-Thienyl)-4-toluenesulfonyl-4,5-dihydro-1,3-oxazole In a manner analogous to Preparation 1, 3-thiophene carboxaldehyde (0.35 mL, 3.99 mmol), tosylmethylisocyanide (0.75 g, 3.84 mmol) and NaCN (0.02 g, 0.40 mmol) gave the desired compound as a tan solid. MS(ES+) m/z 614.8 (2M+H$^+$).

Preparation 3

Preparation of (4R*,5R*)-5-(4-Methoxyphenyl)-4-toluenesulfonyl-4,5-dihydro-1,3-oxazole In a manner analogous to Preparation 1, p-anisaldehyde (0.49 mL, 4.03 mmol), tosylmethylisocyanide (0.75 g, 3.84 mmol) and NaCN (0.02 g, 0.40 mmol) gave the desired compound as a tan solid. MS(ES+) m/z 662.9 (2M+H$^+$).

Preparation 4

Preparation of (4R*,5R*)-5-(3,4-Dichlorophenyl)-4-toluenesulfonyl-4,5-dihydro-1,3-oxazole In a manner analogous to Preparation 1, 3,4-dichlorobenzaldehyde (0.56 g, 3.20 mmol), tosylmethylisocyanide (0.75 g, 3.84 mmol) and NaCN (0.02 g, 0.40 mmol) gave the desired compound as a tan solid. $^1$H NMR (300 MHz, CDCl$_3$) δ 7.85 (d, J=8.3 Hz, 2H), 7.50 (d, J=8.3 Hz, 1H), 7.35 (m, 3H), 7.15 (m, 2H), 6.00 (d, J=6.2 Hz. 1H), 4.96 (dd, J=6.2, 1.7 Hz, 1H), 2.47 (s, 3H).

Preparation 5

Preparation of (4R*,5R*)-4-Toluenesulfonyl-5-[4-(trifluoromethyl)phenyl]-4,5-dihydro-1,3-oxazole In a manner analogous to Preparation 1, 4-(trifluoromethyl)-benzaldehyde (0.54 mL, 3.95 mmol), tosylmethylisocyanide (0.75 g, 3.84 mmol) and NaCN (0.02 g, 0.40 mmol) gave the desired compound as a tan solid. MS(ES+) m/z 411.2 (M+CH$_3$CN$^+$).

Preparation 6

Preparation of (4R*,5R*)-5-Phenyl-4-toluenesulfonyl-4,5-dihydro-1,3-oxazole

In a manner analogous to Preparation 1, benzaldehyde (0.41 mL, 4.03 mmol), tosylmethylisocyanide (0.75 g, 3.84 mmol) and NaCN (0.02 g, 0.40 mmol) gave the desired compound as a tan solid. MS(ES+) m/z 302.2 (M+H$^+$).

Preparation 7

Preparation of 4-Thiophen-3-yl-1H-imidazole

A solution of 4-iodo-1H-imidazole (0.24 g, 1.25 mmol) and Pd(PPh$_3$)$_4$ (72 mg, 0.06 mmol) in DME (12.5 mL) was degased by purging with argon for 10 min. Thiophene-3-boronic acid (0.32 g, 2.50 mmol) and Na2CO3 (2.5 mL of a 2M solution in water) were added. The mixture was heated to reflux for 18 h. After cooling to RT, the solvent was removed under reduced pressure. The residue was subjected to flash chromatography (4% MeOH/CH2Cl2, silica gel) to give 0.16 g of the desired product as an off-white solid. MS(ES+) m/z 151.3 (M+H$^+$).

Preparation 8

Preparation of (4R*,5S*)-5-[4-(tert-Butoxy)phenyl]-4-toluenesulfonyl-4,5-dihydro-1,3-oxazole In a manner analogous to Preparation 1, tosylmethylisocyanide (0.23 g, 1.20 mmol), 4-(tert-butoxy)benzaldehyde (0.23 g, 1.26 mmol) and NaCN (5.9 mg, 0.12 mmol) gave the desired compound as a tan solid. MS(ES+) m/z 374.4 (M+H$^+$).

Preparation 9

Preparation of (4R*,5S*)-5-Benzo[1,3]dioxol-5-yl-4-(toluene-4-sulfonyl)-4,5-dihydro-1,3-oxazole In a manner analogous to Preparation 1, tosylmethylisocyanide (0.23 g, 1.20 mmol), piperonal (0.19 g, 1.26 mmol) and NaCN (5.9 mg, 0.12 mmol) gave the desired compound as a tan solid. MS(ES+) m/z 346.5 (M+H$^+$).

Preparation 10

Preparation of (4R*,5S*)-5-(4-Methylsulfanyl-phenyl)-4-(toluene-4-sulfonyl)-4,5-dihydro-oxazole In a manner analogous to Preparation 1, tosylmethylisocyanide (0.23 g, 1.20 mmol), 4-(methylthio)benzaldehyde (0.19 g, 1.26 mmol), and NaCN (5.9 mg, 0.12 mmol) gave the desired compound as a tan solid. MS(ES+) m/z 348.4 (M+H$^+$).

Preparation 11

Preparation of Dimethyl-{4-[(4R*,5R*)-4-(toluene-4-sulfonyl)-4,5-dihydro-oxazol-5-yl]-phenyl}-amine In a manner analogous to Preparation 1, 4-dimethylaminobenzaldehyde (0.19 g, 1.26 mmol), tosylmethylisocyanide (0.23 g, 1.20 mmol) and NaCN (5.9 mg, 0.12 mmol) gave the desired compound as a tan solid. MS(ES+) m/z 345.5 (M+H$^+$).

Preparation 12

Preparation of (4R*,5R*)-5-(4-Methoxy-3-methyl-phenyl)-4-(toluene-4-sulfonyl)-4,5-dihydro-oxazole In a manner analogous to Preparation 1, 3-methyl-p-anisaldehyde (0.73 mL, 5.25 mmol), tosylmethylisocyanide (0.98 g, 5.00 mmol) and NaCN (24.5 mg, 0.50 mmol) gave the desired compound as a tan solid. MS(ES+) m/z 346.7 (M+H$^+$).

Preparation 13

Preparation of (4R*,5R*)-5-(4-Isopropoxy-phenyl)-4-(toluene-4-sulfonyl)-4,5-dihydro-oxazole In a manner analogous to Preparation 1, isopropylbenzaldehyde (0.68 g, 4.15 mmol), tosylmethylisocyanide (0.77 g, 3.95 mmol) and NaCN (20 mg, 0.40 mmol) gave the desired compound as a tan solid. MS(ES+) m/z 360.6 (M+H$^+$).

Preparation 14

Preparation of (4R*,5R*)-5-(2-Benzyloxy-4-methoxy-phenyl)-4-(toluene-4-sulfonyl)-4,5-dihydro-oxazole In a manner analogous to Preparation 1, 2-benzyloxy-4-methoxybenzaldehyde (2.54 g, 10.5 mmol), tosylmethylisocyanide (1.95 g, 10.0 mmol) and NaCN (49 mg, 1.00 mmol) gave the desired compound as a tan solid. MS(ES+) m/z 438.5 (M+H$^+$).

Preparation 15

Preparation of (4R*,5R*)-5-(2-Methoxy-phenyl)-4-(toluene-4-sulfonyl)-4,5-dihydro-oxazole In a manner analogous to Preparation 1, 0-anisaldehyde (053 mL, 5.25 mmol), tosylmethylisocyanide (0.98 g, 5.0 mmol) and NaCN (24.5 mg, 0.50 mmol) gave the desired compound as a tan solid. MS(ES+) m/z 332.0 (M+H$^+$).

Preparation 16

Preparation of (4R*,5R*)-5-(4-Methoxy-2-methoxymethoxy-phenyl)-4-(toluene-4-sulfonyl)-4,5-dihydro-oxazole In a manner analogous to Preparation 1, 4-methoxy-2-methoxymethoxybenzaldehyde (0.12 g, 0.63 mmol), tosylmethylisocyanide (0.12 g, 0.60 mmol) and NaCN (3 mg, 0.06 mmol) gave the desired compound as a tan solid. MS(ES+) m/z 392.0 (M+H$^+$).

Preparation 17

Preparation of (4R*,5R*)-5-(4-Fluoro-phenyl)-4-(toluene-4-sulfonyl)-4,5-dihydro-oxazole In a manner analogous to Preparation 1, 4-fluorobenzaldehyde (0.18 g, 1.47 mmol), tosylmethylisocyanide (0.27 g, 1.40 mmol) and NaCN (6.9 mg, 0.14 mmol) gave the desired compound as a tan solid. MS(ES+) m/z 320.6 (M+H$^+$).

Preparation 18

Preparation of (4R*,5R*)-4-(Toluene-4-sulfonyl)-5-(3-trifluoromethyl-phenyl)-4,5-dihydro-oxazole In a manner analogous to Preparation 1, 3-(trifluoromethyl)benzaldehyde (0.16 g, 1.47 mmol), tosylmethylisocyanide (0.27 g, 1.40 mmol) and NaCN (6.9 mg, 0.14 mmol) gave the desired compound as a tan solid. $^1$H NMR (300 MHz, CDCl3) δ 2.44 (s, 3H), 4.98–5.04 (dd, 1H), 6.08–6.12 (dd, 1H), 7.3–7.42 (d, 2H), 7.50–7.62 (m, 5H), 7.78–7.86 (d, 2H).

Preparation 19

Preparation of (4R*,5R*)-5-(2-Fluoro-5-trifluoromethyl-phenyl)-4-(toluene-4-sulfonyl)-4,5-dihydro-oxazole In a manner analogous to Preparation 1, 2-fluoro-5-(trifluoromethyl)benzaldehyde (0.26 g, 1.47 mmol), tosylmethylisocyanide (0.27 g, 1.40 mmol) and NaCN (6.9 mg, 0.14 mmol) gave the desired compound as a tan solid. $^1$H NMR (300 MHz, CDCl3) δ 2.48 (s, 3H), 5.10–5.14 (dd, 1H), 6.12–6.16 (dd, 1H), 7.16–7.20 d, 2H), 7.40–7.44 (dd, 2H), 7.52–7.56 (d, 1H), 7.66–7.70 (d, 1H), 7.88–7.92 (dd, 2H).

Preparation 20

Preparation of (4R*,5R*)-5-(4-Chloro-3-trifluoromethy-phenyl)-4-(toluene-4-sulfonyl)-4,5-dihydro-oxazole In a manner analogous to Preparation 1, 4-chloro-3-(trifluoromethyl)benzaldehyde (0.31 g, 1.47 mmol), tosylmethylisocyanide (0.27 g, 1.40 mmol) and NaCN (6.9 mg, 0.14 mmol) gave the desired compound as a tan solid. MS(ES+) m/z 404.5 (M+H$^+$).

Preparation 21

Preparation of (4R*,5R*)-5-(3-Chloro-4-nitro-phenyl)-4-(toluene-4-sulfonyl)-4,5-dihydro-oxazole In a manner analogous to Preparation 1, tosylmethylisocyanide (0.30 g, 1.52 mmol), 4-chloro-3-nitrobenzaldehyde (0.30 g, 1.60 mmol) and NaCN (10 mg, 0.20 mmol) gave the desired compound as a tan solid. $^1$H NMR (300 MHz, CDCl3) δ 7.85 (m, 3H), 7.60 (m, 2H), 7.40 (d, J=10.7 Hz, 2H), 7.23 (s, 2H), 6.10 (d, J=6.4 Hz, 1H), 4.95 (m, 1H), 2.48 (s, 3H).

Preparation 22

Preparation of (4R*,5R*)-5-(2,4-Difluoro-phenyl)-4-(toluene-4-sulfonyl))-4,5-dihydro-oxazole In a manner analogous to Preparation 1, tosylmethylisocyanide (0.30 g, 1.52 mmol), 2,4-difluorobenzaldehyde (0.18 mL, 1.60 mmol) and NaCN (10 mg, 0.20 mmol) gave the desired compound as a tan solid. MS(ES+) m/z 338.5 (M+H$^+$).

Preparation 23

Preparation of (4R*,5R*)-5-(4-Chloro-3-fluoro-phenyl)-4-(toluene-4-sulfonyl)-4,5-dihydro-oxazole In a manner analogous to Preparation 1, tosylmethylisocyanide (0.30 g, 1.52 mmol), 4-chloro-3-fluorobenzaldehyde (0.25 g, 1.60 mmol) and NaCN (10 mg, 0.20 mmol) gave the desired compound as a tan solid. MS(ES+) m/z 373.5 (M+Na$^+$).

The following examples illustrate methods for preparing the biologically active compounds of this invention from intermediate compounds such as those described in the foregoing Preparations.

Examples 1–20

The compounds of Example 1–20 were prepared as part of a solution-phase combinatorial array.

The compound of Preparation 1 (3.84 mmol) was suspended in toluene (6.40 mL) and equally divided into 6 reaction vessels. Benzyl amine (0.08 mL, 0.80 mmol), 4-methylbenzylamine (0.10 mL, 0.80 mmol), 4-chlorobenzylamine (0.10 mL, 0.8 mmol), 3,4-dichlorobenzylamine (0.11 mL, 0.80 mmol), 4-methoxybenzylamine (0.11 mL, 0.80 mmol) and 4-(trifluoromethyl)benzylamine (0.11 mL, 0.80 mmol) were added to 1 each of the 8 reaction vessels. The reaction vessels were sealed and heated to 105° C. for 18 h. After allowing the reactions to cool to room temperature, the solvent was removed under reduced pressure. Each product was isolated by preparative reverse phase HPLC (10% to 95% CH3CN/H2O+0.1% TFA over 15 min.).

In a similar fashion, the compound of Preparations 2 (3.84 mmol), 3 (3.84 mmol), 4 (3.84 mmol), 5 (3.84 mmol) and 6 (3.84 mmol) were reacted with benzyl amine (0.08 mL, 0.80 mmol), 4-methylbenzylamine (0.10 mL, 0.80 mmol), 4-chlorobenzylamine (0.10 mL, 0.8 mmol), 3,4-dichlorobenzylamine (0.11 mL, 0.80 mmol), 4-methoxybenzylamine (0.11 mL, 0.80 mmol) and 4-(trifluoromethyl)benzylamine (0.11 mL, 0.80 mmol).

| Example | Compound Name | MS (ES+) m/z (M + H$^+$) |
|---|---|---|
| 1 | 1-Benzyl-4-(2-thienyl)-1H-imidazole | 241.0 |
| 2 | 1-Benzyl-4-(3-thienyl)-1H-imidazole | 241.1 |
| 3 | 1-Benzyl-4-(4-methoxyphenyl)-1H-imidazole | 265.1 |
| 4 | 1-Benzyl-4-(4-trifluoromethylphenyl)-1H-imidazole | 303.1 |
| 5 | 1-(4-Methylbenzyl)-4-(2-thienyl)-1H-imidazole | 255.0 |
| 6 | 1-(4-Methylbenzyl)-4-(3-thienyl)-1H-imidazole | 255.0 |

-continued

| Example | Compound Name | MS (ES+) m/z (M + H+) |
|---|---|---|
| 7 | 4-(4-Methoxyphenyl)-1-(4-methylbenzyl)-1H-imidazole | 279.4 |
| 8 | 1-(4-Methylbenzyl)-4-phenyl-1H-imidazole | 249.1 |
| 9 | 1-(4-Chlorobenzyl)-4-(2-thienyl)-1H-imidazole | 274.9 |
| 10 | 1-(4-Chlorobenzyl)-4-(3-thienyl)-1H-imidazole | 275.0 |
| 11 | 1-(4-Chlorobenzyl)-4-(4-methoxyphenyl)-1H-imidazole | 299.1 |
| 12 | 1-(4-Chlorobenzyl)-4-(3,4-dichlorophenyl)-1H-imidazole | 337.0 |
| 13 | 1-(4-Chlorobenzyl)-4-[4-(trifluoromethyl)phenyl]-1H-imidazole | 337.1 |
| 14 | 1-(4-Chlorobenzyl)-4-phenyl-1H-imidazole | 269.0 |
| 15 | 1-(3,4-Dichlorobenzyl)-4-(2-thienyl)-1H-imidazole | 308.9 |
| 16 | 1-(3,4-Dichlorobenzyl)-4-[4-(trifluoromethyl)phenyl]-1H-imidazole | 371.0 |
| 17 | 1-(3,4-Dichlorobenzyl)-4-phenyl-1H-imidazole | 303.0 |
| 18 | 1-(4-Methoxybenzyl)-4-(3-thienyl)-1H-imidazole | 271.2 |
| 19 | 1-(4-Methoxybenzyl)-4-(4-methoxyphenyl)-1H-imidazole | 295.1 |
| 20 | 4-(3,4-Dichlorophenyl)-1-[4-(trifluoromethyl)benzyl]-1H-imidazole | 370.9 |

Examples 21–33

The compounds of Examples 21–33 were prepared as part of a solution-phase combinatorial array.

The compound of Preparation 8 (0.20 mmol) was suspended in toluene (1.0 mL) and (4-aminomethyl-phenyl)-dimethyl-amine (0.12 g, 0.80 mmol) was added. The reaction vessel was sealed and heated to 105° C. for 18 h. After allowing the reactions to cool to room temperature, the solvent was removed under reduced pressure. The mixture was then treated with TFA (0.2 ml, 30% in CH$_2$Cl$_2$) for 4 hrs. The solvent was removed and the product was isolated by preparative reverse phase HPLC (10% to 90% CH$_3$CN/H$_2$O+0.1% TFA over 15 min.).

In a similar fashion, but omitting the TFA treatment, the compound of Preparations 2 (0.20 mmol) and Preparation 3 (0.20 mmol) were reacted with naphthalen-2-yl-methylamine (0.126 g, 0.8 mmol), and the compound of Preparation 4 (0.15 mmol) was reacted with 2,4-dichlorobenzylamine (0.08 ml, 0.60 mmol).

| Example | Compound Name | MS (ES+) m/z (M + H+) |
|---|---|---|
| 21 | 1-Benzo[1,3]dioxol-5-ylmethyl-4-thiophen-3-yl-1H-imidazole | 285.1 |
| 22 | 4-[4-(4-Dimethylamino-phenyl)-imidazol-1-ylmethyl]-aniline | 321.2 |
| 23 | 4-[1-(4-Dimethylamino-benzyl)-1H-imidazol-4-yl]-phenol | 294.2 |
| 24 | 4-[4-(4-Methoxy-3-methyl-phenyl)-imidazol-1-ylmethyl]-phenol | 295.1 |
| 25 | 4-[4-(4-Dimethylamino-phenyl)-imidazol-1-ylmethyl]-phenol | 294.2 |
| 26 | (4-[1-(4-Isopropoxy-benzyl)-1H-imidazol-4-yl]-phenyl}-dimethyl-amine | 336.2 |
| 27 | Dimethyl-[4-(1-naphthalen-2-ylmethyl-1H-imidazol-4-yl)-phenyl]-amine | 328.2 |
| 28 | 1-Naphthalen-2-ylmethyl-4-thiophen-3-yl-1H-imidazole | 291.1 |
| 29 | 4-Benzo[1,3]dioxol-5-yl-1-naphthalen-2-ylmethyl-1H-imidazole | 329.1 |
| 30 | 4-(4-Methylsulfanyl-phenyl)-1-naphthalen-2-ylmethyl-1H-imidazole | 331.6 |
| 31 | 4-(2-Methoxy-phenyl)-1-naphthalen-2-ylmethyl-1H-imidazole | 315.4 |
| 32 | 4-(4-Thiophen-3-yl-imidazol-1-ylmethyl)-phenylamine | 256.1 |
| 33 | 4-[4-(4-Isopropoxy-phenyl)-imidazol-1-ylmethyl]-phenylamine | 308.2 |

Examples 34–38

The compounds of Examples 34–38 were prepared as part of a solution-phase combinatorial array.

The compound of Preparation 14 (0.45 mmol) was suspended in toluene (3 mL) and equally divided into 3 reaction vessels. 2-(4-Methoxy-phenyl)-ethylamine (0.15 mmol), 4-methoxyphenylamine (0.15 mmol) and 2,4-dichloro-benzylamine (0.15 mmol) were added to 1 each of the 3 reaction vessels. The reaction vessels were sealed and heated to 105° C. for 18 h. After allowing the reactions to cool to room temperature, the solvent was removed under reduced pressure. Each product was isolated by preparative reverse phase HPLC (10% to 95% CH3CN/H2O+0.1% TFA over 15 min.).

The compound of Preparation 16 (0.45 mmol) was suspended in toluene (3 mL) and equally divided into 3 reaction vessels. 2-(4-Methoxy-phenyl)-ethylamine (0.15 mmol), 4-methoxyphenylamine (0.15 mmol) and 2,4-dichloro-benzylamine (0.15 mmol) were added to 1 each of the 3 reaction vessels. The reaction vessel was sealed and heated to 105° C. for 18 h. After allowing the reactions to cool to room temperature, the solvent was removed under reduced pressure. The mixture was then treated with TFA (0.2ml, 30% in CH$_2$Cl$_2$) for 4 hrs. The solvent was removed and the product was isolated by preparative reverse phase HPLC (10% to 90% CH$_3$CN/H$_2$O+0.1% TFA over 15 min.).

| Example | Compound Name | MS (ES+) m/z (M + H+) |
|---|---|---|
| 34 | 5-Methoxy-2-{1-[2-(4-methoxy-phenyl)-ethyl]-1H-imidazol-4-yl}-phenol | 325.2 |
| 35 | 4-(2-Benzyloxy-4-methoxy-phenyl)-1-(4-methoxy-phenyl)-1H-imidazole | 387.6 |
| 36 | 5-Methoxy-2-[1-(4-methoxy-phenyl)-1H-imidazol-4-yl]-phenol | 297.6 |
| 37 | (2-Benzyloxy-4-methoxy-phenyl)-1-(2,4-dichloro-benzyl)-1H-imidazole | 439.1 |
| 38 | 2-[1-(2,4-Dichloro-benzyl)-1H-imidazol-4-yl]-5-methoxy-phenol | 349.1 |

Example 39

Preparation of 4-(3-Chloro-4-nitro-phenyl)-1-(1,2-diphenyl-ethyl)-1H-imidazole 1,2-Diphenylethylamine (0.16 g 0.8 mmol) in toluene (1 mL) was added to the compound of Preparation 21 (0.2 mmol) in toluene (1 mL). The reaction was heated to 90° C. for 18 h. After the reaction was allowed to cool to RT, the solvent was removed under vacuum. Preparative reverse phase HPLC (10% to 90% CH$_3$CN/H$_2$O+0.1% TFA over 15 min.) gave 11 mg of the desired material as a yellow oil. MS(ES+) m/z 404.0 (M+H+).

Example 40

Preparation of 4-(2,4-Difluoro-phenyl)-1-(4-trifluoromethoxy-benzyl)-1H-imidazole 4-Trifluoromethoxybenzylamine (0.15 g, 0.8 mmol) in toluene (1 mL) was added to the compound of Preparation 22 (0.2 mmol). The reaction was heated to 90° C. for 18 h. After the reaction was allowed to cool to RT, the solvent was removed under vacuum. Preparative reverse phase HPLC (10% to 90% $CH_3CN/H_2O+0.1\%$ TFA over 15 min.) gave 5.8 mg of the desired material as a yellow oil. MS(ES+) m/z 355.0 (M+H$^+$).

Example 41

Preparation of 4-(4-Chloro-3-fluoro-phenyl)-1-(4-methyl-benzyl)-1H-imidazole 2-(p-Tolyl)ethylamine (0.11 g, 0.8 mmol) in toluene (1 mL) was added to the compound of Preparation 23 (0.2 mmol) in toluene (1 mL). The reaction was heated to 90° C. for 18 h. After the reaction was allowed to cool to RT, the solvent was removed under vacuum. Preparative reverse phase HPLC (10% to 90% $CH_3CN/H_2O+0.1\%$ TFA over 15 min.) gave 10.9 mg of the desired material as a yellow oil. MS(ES+) m/z 315.0 (M+H$^+$).

Examples 42–46

The compounds of Examples 42–46 were prepared as part of a solution phase combinatorial array.

The compound of Preparation 17 (0.40 mmol) was suspended in toluene (2 mL) and equally divided into 2 reaction vessels. 4-Chloro-3-(trifluoromethyl)benzylamine (0.20 mmol) and 4-fluorobenzylamine (0.20 mmol) were added to 1 each of the 2 reaction vessels. The reaction vessels were sealed and heated to 105° C. for 18 h. After allowing the reactions to cool to room temperature, the solvent was removed under reduced pressure. Each product was isolated by preparative reverse phase HPLC (10% to 95% CH3CN/ H2O+0.1% TFA over 15 min.).

In a similar fashion, the compound of Preparation 18 (0.40 mmol). Preparation 19 (0.40 mml) and Preparation 20 (0.40 mmol) were reacted with 4-chloro-3-(trifluoromethyl) benzylamine (0.20 mmol) and 4-fluorobenzylamine (0.20 mmol).

| Example | Compound Name | MS (ES+) m/z (M + H$^+$) |
|---|---|---|
| 42 | 1-(4-Chloro-3-trifluoromethyl-benzyl)-4-(4-fluoro-phenyl)-1H-imidazole | 355.1 |
| 43 | 1-(4-Chloro-3-trifluoromethyl-benzyl)-4-(3-trifluoromethyl-phenyl)-1H-imidazole | 405.1 |
| 44 | 1-(4-Chloro-3-trifluoromethyl-benzyl)-4-(2-fluoro-3-trifluoromethyl-phenyl)-1H-imidazole | 423.0 |
| 45 | 1-(4-Fluoro-benzyl)-4-(3-trifluoromethyl-phenyl)-1H-imidazole | 321.6 |
| 46 | 4-(4-Chloro-3-trifluoromethyl-phenyl)-1-(2-fluoro-5-trifluoromethyl-benzyl)-1H-imidazole | 423.0 |

Example 47

Preparation of 1-[3-(4-Methoxy-phenyl)-propyl]-4-thiophen-3-yl-1H-imidazole

Methanesulfonyl chloride (0.46 mL, 6.00 mmol) was added to a solution of 3-(p-methoxyphenyl)propanol (0.83 g, 5.00 mmol) and Et$_3$N (1.40 mL, 10.0 mmol) in $CH_2Cl_2$ (10 mL) at 0° C. After 4 h at 0° C., the reaction was diluted with $CH_2Cl_2$ and washed with cold brine and dried over $MgSO_4$. The solvent was removed under reduced pressure to give the corresponding mesylate as a light yellow oil. The mesylate (0.37 g, 1.53 mmol) was added to a stirred mixture of 4-(thien-3-yl)-1H-imidazole (0.22 g, 1.46 mmol. compound of Preparation 7) and $K_2CO_3$ (0.40 g, 2.92 mmol) in DMF (10 mL). The reaction was heated to 80° C. for 18 h. After allowing to cool to RT, the reaction was filtered and the filtrate was concentrated in vacuo. Flash chromatography (1% $MeOH/CH_2Cl_2$, silica gel) afforded 70 mg of the desired product as a light brown oil. MS(ES+) m/z 298.9 (M+H$^+$); Anal. ($C_{17}H_{18}N_2OS.0.6H_2O$) calcd: C, 66.04: H, 6.26: N, 9.06. found: C, 65.79: H, 5.92; N, 8.87.

Example 48

Preparation of 2-(2,4-Dichloro-benzyl)-5-(2,4-dimethoxy-phenyl)-1H-imidazole a) 2-(2,4-Dichloro-phenyl)-acetamidine A solution of 2,4-dichlorobenzonitrile (5.00 g, 26.9 mmol) in EtOH (25 mL) at 0° C. was saturated with HCl gas. The solution was allowed to warm to RT. After 18 h, the solvent was removed under reduced pressure and the white residue was suspended in EtOH (50 mL) and cooled to 0° C. Ammonia gas was bubbled through the suspension for 15 min. The mixture was allowed to warm to RT overnight. The solvent was removed under reduced pressure and the residue was partitioned between water and CHCl$_3$. The aqueous layer was separated and the pH was adjusted to 10 with 1N NaOH. The aqueous layer was extracted with CHCl$_3$. The organic extract was concentrated in vacuo to give 0.39 g of the desired material as a white solid. This was used without further purification. MS(ES+) m/z 203.4 (M+H$^+$).

b) 2-(2,4-Dichloro-benzyl)-5-(2,4-dimethoxy-phenyl)-1H-imidazole

A solution of the compound of Example 48(a) (0.10 g, 0.49 mmol) in CHCl$_3$ (1 mL) was added dropwise to 2-bromo-1-(2,4-dimethoxy-phenyl)-ethanone (45 mg, 0.17 mmol) in CHCl$_3$ (0.20 mL). After stirring at RT for 18 h, the solvent was removed under vacuum. The residue was subjected to radial chromatography (5% MeOH/CHCl$_3$, 6 mm plate, silica gel) to give 25 mg of the desired product as a yellow oil. Anal. ($C_{18}H_{16}Cl_2N_2O_2.0.5H_2O.0.5HBr$) calcd: C, 52.39; H, 4.27; N, 6.79. found: C, 52.45; H, 4.22; N, 6.72.

Example 49

Preparation of 2-(3.4-Dichloro-benzyl)-4-(3,4-dichloro-phenyl)-1H-imidazole a) 2-(3,4-Dichloro-phenyl)-acetamidine In a manner analogous to Example 48(a), 3,4-dichloroacetonitrile (5.00 g, 26.9 mmol) gave 6.64 g of the desired material as a white solid. MS(ES+) m/z 203.4 (M+H$^+$).

b) 2-(3,4-Dichloro-benzyl)-4-(3,4-dichloro-phenyl)-1H-imidazole

In manner analogous to Example 48(b), the compound of Example 49(a) (0.80 g, 3.94 mmol) and 2-bromo-1-(3,4-dichloro-phenyl)-ethanone (0.53 g 1.98 mmol) gave 78 mg of the desired material as a tan powder after radial chromatography (40% EtOAc/hexanes, 6 mm plate. silica gel). Anal. ($C_{16}H_{10}Cl_4N_2.0.60H_2O$) calcd: C, 50.19; H, 2.95; N, 7.32. found: C, 50.45; H, 2.96; N, 6.94.

Example 50

Preparation of 3,4-Dichlorophenylmethyl-4-(4-trifluoromethyl-phenyl)-1H-imidazole In a manner analogous to Example 48(b), the compound of Example 55(a) (0.48 g, 2.36 mmol) and 2-bromo-1-(4- trifluoromethyl-phenyl)-ethanone (0.32 g, 1.20 mmol) gave 42 mg of the desired material as a yellow oil after flash chromatography (40% EtOAc.hexanes, silica gel). MS(ES+) m/z 371.5 (M+H$^+$).

Example 51

Preparation of 5-(2,4-Dichloro-phenyl)-2-(4-trifluoromethyl-benzyl)-1H-imidazole In a manner analogous to Example 48(b), 2-bromo-1-(2, 4-dichloro-phenyl)-ethanone (0.15 g, 1.98 mmol) and 2-(4-trifluoromethyl-phenyl)-acetamidine (0.22 g, 1.09 mmol) gave 0.10 g of the desired material as a yellow oil after flash chromatography (30% EtOAc/hexane, silica gel). MS(ES+) m/z 371.5 (M+H$^+$).

Examples 52–77

The compounds of Examples 52–77 were prepared as part of a solution-phase combinatorial array.

A solution of 2-(2,4-dichloro-phenyl)-acetamidine (2.80 mmol) in CHCl$_3$ (2.8 mL) was equally divided into 7 reaction vessels. 2-Bromo-1-(2,4-dimethoxy-phenyl) ethanone (0.2 mL, 1M in CHCl$_3$, 0.2 mmol), 2-bromo-1-phenyl-ethanone (0.2 mL, 1M in CHCl$_3$, 0.2 mmol), 2-bromo-1-(4-methoxy-phenyl)-ethanone (0.2 mL, 1M in CHCl$_3$, 0.2 mmol), 2-bromo-1-p-tolyl-ethanone (0.2 mL, 1M in CHCl$_3$, 0.2 mmol), 2-bromo-1-(3,4-dichloro-phenyl)-ethanone (0.2 mL, 1M in CHCl$_3$, 0.2 mmol), 2-bromo-1-(4-fluoro-phenyl)-ethanone (0.2 mL, 1M in CHCl$_3$, 0.2 mmol) and 2-bromo-1-(4-trifluoromethyl-phenyl)-ethanone (0.2 mL, 1M in CHCl$_3$, 0.2 mmol) were added to 1 each of the 7 reaction vessels. After agitating at RT for 18 h. the solvent was removed under reduced pressure. Each product was isolated by preparative reverse phase HPLC (10% to 95% CH$_3$CN/H$_2$O+0.1% TFA over 15 min.).

In a similar fashion, 2-(3,4-dichloro-phenyl)-acetamidine (3.60 mmol) was reacted with 2-bromo-1-phenyl-ethanone (0.2 mL, 1M in CHCl$_3$, 0.2 mmol), 2-bromo-1-(4-methoxy-phenyl)-ethanone (0.2 mL, 1M in CHCl$_3$, 0.2 mmol), 1-biphenyl-4-yl-2-bromo-ethanone (0.2 mL, 1M in CHCl$_3$, 0.2 mmol), 2-bromo-1-p-tolyl-ethanone (0.2 mL, 1M in CHCl$_3$, 0.2 mmol), 2-bromo-1-(2,4-dichloro-phenyl)-ethanone (0.2 mL, 1M in CHCl$_3$, 0.2 mmol), 2-bromo-1-naphthalen-1-yl-ethanone (0.2 mL, 1M in CHCl$_3$, 0.2 mmol), 2-bromo-1-(3,4-dichloro-phenyl)-ethanone (0.2 mL, 1M in CHCl$_3$, 0.2 mmol), 2-bromo-1-(4-fluoro-phenyl)-ethanone (0.2 mL, 1M in CHCl$_3$, 0.2 mmol) and 2-bromo-1-(4-trifluoromethyl-phenyl)-ethanone (0.2 mL, 1M in CHCl$_3$, 0.2 mmol).

Similarly, 2-(4-trifluoromethyl-phenyl)-acetamidine (1.60 mmol) was reacted with 2-bromo-1-(2,4-dichloro-phenyl)-ethanone (0.2 mL, 1M in CHCl$_3$, 0.2 mmol), 2-bromo-1-naphthalen-1-yl-ethanone (0.2 mL, 1M in CHCl$_3$, 0.2 mmol), 2-bromo-1-(3,4-dichloro-phenyl)-ethanone (0.2 mL, 1M in CHCl$_3$, 0.2 mmol) and 2-bromo-1-(4-fluoro-phenyl)-ethanone (0.2 mL, 1M in CHCl$_3$, 0.2 mmol).

Similarly, 2-biphenyl-4-yl-acetamidine (1.20 mmol) was reacted with 2-bromo-1-p-tolyl-ethanone (0.2 mL, 1M in CHCl$_3$, 0.2 mmol). 2-bromo-1-(3,4-dichloro-phenyl)-ethanone (0.2 mL, 1M in CHCl$_3$, 0.2 mmol) and 2-bromo-1-(4-trifluoromethyl-phenyl)-ethanone (0.2 mL, 1M in CHCl$_3$, 0.2 mmol).

Similarly, 2-benzo[1,3]dioxol-5-yl-acetamidine (1.20 mmol) was reacted with 2-bromo-1-(2,4-dichloro-phenyl)-ethanone (0.2 mL, 1M in CHCl$_3$, 0.2 mmol), 2-bromo-1-naphthalen-1-yl-ethanone (0.2 mL, 1M in CHCl$_3$, 0.2 mmol) and 2-bromo-1-(3,4-dichloro-phenyl)-ethanone (0.2 mL, 1M in CHCl$_3$, 0.2 mmol).

Similarly, 2-(4-methoxy-phenyl)-acetamidine (0.4 mmol) was reacted with 2-bromo-1-(2,4-dichloro-phenyl)-ethanone (0.2 mL, 1M in CHCl$_3$, 0.2 mmol) and 2-p-tolyl-acetamidine (0.4 mmol) was reacted with 2-bromo-1-(2,4-dichloro-phenyl)-ethanone (0.2 mL, 1M in CHCl$_3$, 0.2 mmol).

| Example | Compound Name | MS (ES+) m/z (M + H$^+$) |
|---|---|---|
| 52 | 2-(2,4-Dichloro-benzyl)-5-phenyl-1H-imidazole | 302.0 |
| 53 | 2-(2,4-Dichloro-benzyl)-5-(4-methoxy-phenyl)-1H-imidazole | 332.0 |
| 54 | 2-(2,4-Dichloro-benzyl)-5-p-tolyl-1H-imidazole | 316.0 |
| 55 | 2-(2,4-Dichloro-benzyl)-5-(3,4-dichloro-phenyl)-1H-imidazole | 369.8 |
| 56 | 2-(2,4-Dichloro-benzyl)-5-(4-fluoro-phenyl)-1H-imidazole | 320.0 |
| 57 | 2,4-Dichlorophenylmethyl-5-(4-trifluoromethyl-phenyl)-1H-imidazole | 370.0 |
| 58 | 2-(3,4-Dichloro-benzyl)-5-phenyl-1H-imidazole | 302.0 |
| 59 | 2-(3,4-Dichloro-benzyl)-5-(4-methoxy-phenyl)-1H-imidazole | 333.6 |
| 60 | 5-Biphenyl-4-yl-2-(3,4-dichloro-benzyl)-1H-imidazole | 378.0 |
| 61 | 2-(3,4-Dichloro-benzyl)-5-p-tolyl-1H-imidazole | 316.0 |
| 62 | 2-(3,4-Dichloro-benzyl)-5-(2,4-dichloro-phenyl)-1H-imidazole | 369.8 |
| 63 | 2-(3,4-Dichloro-benzyl)-5-naphthalen-2-yl-1H-imidazole | 352.0 |
| 64 | 2-(3,4-Dichloro-benzyl)-5-(4-fluoro-phenyl)-1H-imidazole | 320.0 |
| 65 | 5-Naphthalen-2-yl-2-(4-trifluoromethyl-benzyl)-1H-imidazole | 352.0 |
| 66 | 5-(3,4-Dichloro-phenyl)-2-(4-trifluoromethyl-benzyl)-1H-imidazole | 370.0 |
| 67 | 5-(4-Fluoro-phenyl)-2-(4-trifluoromethyl-benzyl)-1H-imidazole | 321.0 |
| 68 | 5-(2,4-Dichloro-phenyl)-2-(4-methyl-benzyl)-1H-imidazole | 316.0 |
| 69 | 2-Biphenyl-4-ylmethyl-5-p-tolyl-1H-imidazole | 324.2 |
| 70 | 2-Biphenyl-4-ylmethyl-5-(3,4-dichloro-phenyl)-1H-imidazole | 378.0 |
| 71 | 2-Bipbenyl-4-ylmethyl-5-(4-trifluoromethyl-phenyl)-1H-imidazole | 378.0 |
| 72 | 2-Benzo[1,3]dioxol-5-ylmethyl-5-(2,4-dichloro-phenyl)-1H-imidazole | 346.0 |
| 73 | 2-Benzo[1,3]dioxol-5-ylmethyl-5-naphthalen-2-yl-1H-imidazole | 328.0 |
| 74 | 2-Benzo[1,3]dioxol-5-ylmethyl-5-(3,4-dichloro-phenyl)-1H-imidazole | 346.0 |
| 75 | 5-(2,4-Dichloro-phenyl)-2-(4-methoxy-benzyl)-1H-imidazole | 333.5 |
| 76 | 2-(4-Trifluoromethyl-benzyl)-5-(4-trifluoro-methyl-phenyl)-1H-imidazole | 371.6 |
| 77 | 2-Benzo[1,3]dioxol-5-ylmethyl-5-p-tolyl-1H-imidazole | 293.7 |

Example 78

Preparation of 1-(2,4-Dichloro-benzyl)-4-thiophen-3-yl-1H-imidazole

The compound of Preparation 2 (0.77 g, 2.50 mmol) and 2,4-dichlorobenzyl amine (1.35 mL, 10.0 mmol) in toluene (15 mL) was heated at 105° C. overnight. The solvent was removed under vacuum and the residue was partitioned between EtOAc and 10% NaHCO$_3$. The organic layer was washed with brine, dried over MgSO$_4$ and concentrated. Flash chromatography (0.7% CH$_3$OH/CH$_2$Cl$_2$) gave 0.18 g of the desired product as a light tan solid. MS(ES+) m/z 309.5 (M+H$^+$). Anal. (C$_{14}$H$_{10}$N$_2$Cl$_2$S.0.8H$_2$O) calcd: C, 51.96; H, 3.61; N, 8.66. found: C, 51.94; H, 3.31; N, 8.38.

Example 79

Preparation of 1-(3-Methyl-benzyl)-4-thiophen-3-yl-1H-imidazole

The compound of Preparation 7 (0.17 g, 1.11 mmol), 3-methylbenzylbromide (0.23 g, 1.24 mmol) and potassium carbonate (0.31 g, 2.24 mmol) were combined in DMF (5 mL). After 2 days at RT, the reaction mixture was diluted with 50% brine and extracted with EtOAc. The combined organic extracts were dried over $Na_2SO_4$ and concentrated under reduced pressure. Radial chromatography (50% EtOAc/hexanes, silica gel. 6 mm plate) gave 0.06 g of the desired material as a yellow oil. Anal. ($C_{15}H_{14}N_2S.0.5H_2O$) calcd: C, 68.41: H, 5.74: N, 10.64. found: C, 68.71; H, 5.57; N, 10.49.

Example 80

Preparation of 1-(2-Methyl-benzyl)-4-thiophen-3-yl-1H-imidazole

The compound of Preparation 7 (0.14 g, 0.95 mmol), 2-methylbenzylbromide (0.19 g, 1.02 mmol) and potassium carbonate (0.26 g, 1.88 mmol) were combined in DMF (5 mL). After 2 days at RT, the reaction mixture was diluted with 50% brine and extracted with EtOAc. The combined organic extracts were dried over $Na_2SO_4$ and concentrated under reduced pressure. Radial chromatography (50% EtOAc/hexanes, silica gel, 6 mm plate) gave 0.07 g of the desired material as a yellow oil. Anal. ($C_{15}H_{14}N_2S.0.25H_2O$) calcd: C, 69.60; H, 5.65: N, 10.82. found: C, 69.63; H, 5.51; N, 10.61.

Example 81

Preparation of 1-(2-Nitro-benzyl)-4-thiophen-3-yl-1H-imidazole

The compound of Preparation 7 (0.33 g, 2.23 mmol) and $K_2CO_3$ (0.62 g, 4.46 mmol) in DMF (10 mL) was stirred at RT for 20 min. 2-Nitrobenzylchloride (0.40 g, 2.34 mmol) was added and the resulting mixture was stirred at RT for 18 h. The solvent was removed under reduced pressure. The residue was taken up in $CH_2Cl_2$ and filtered. The filter cake was washed with $CH_2Cl_2$ and the solvent was removed from the combined filtrates under reduced pressure. Flash chromatography (0.75% $CH_3OH/CH_2Cl_2$, silica gel) gave 0.18 g of the desired material as a light tan solid. MS(ES+) m/z 285.9 (M+H$^+$). Anal. ($C_{14}H_{11}N_3O_2S.0.25H_2O$) calcd: C, 58.02; H, 4.00; N, 14.50. found: C, 58.39; H, 3.75; N, 14.16.

Example 82

Preparation of 1-Biphenyl-3-ylmethyl-4-thiophen-3-yl-1H-imidazole

In a manner analogous to Example 81, the compound of Preparation 7 (0.15 g, 1.0 mmol), $K_2CO_3$ (0.28 g, 2.00 mmol) and 3-bromomethylbiphenyl (0.26 g, 1.05 mmol) gave 60 mg of the desired material as a beige solid. MS(ES+) m/z 317.1 (M+H$^+$). Anal. ($C_{20}H_{16}N_2S.0.30H_2O$) calcd: C, 74.64; H, 5.20 N, 8.70. found: C, 74.56; H, 5.11 N, 8.49.

Example 83

Preparation of 4-Thiophen-3-yl-1-(3-m-tolyl-propyl)-1H-imidazole a) Methanesulfonic Acid 3-m-Tolyl-propyl Ester
3-(m-Methylphenyl)-1-propanol (0.45 g, 3.00 mmol), MsCl(278 uL, 3.60 mmol) and Et3N (0.84 mL, 6.00 mmol) were combined in CH2Cl2 (30 mL) and stirred at 0° C. for 4 hrs. The reaction was then diluted with CH2Cl2 (30 mL) and washed with cold brine, dried over Na2SO4 and concentrated to give a light brown oil. This was used without further purification. 1H NMR (300 MHz, CDCl3) δ 2.04–2.09 (m, 2H), 2.33(s, 3H), 2.69–2.74 (t, 2H), 2.99 (s, 3H), 4.20–4.24 (t, 2H), 6.97–7.04 (m, 3H), 7.16–7.19 (m, 1H).

b) 4-Thiophen-3-yl-1-(3-m-tolyl-propyl)-1H-imidazole
A mixture of the compound of Preparation 7 (0.17 g, 1.15 mmol) and NaH (69 mg, 60% dispersion in mineral oil, 1.73 mmol) in THF(20 mL) was stirred at 0° C. for 20 min. The compound of Example 83(a) (0.28 g, 1.20 mmol) was added and the resulting mixture was heated to reflux overnight. After allowing the reaction to cool to RT, the reaction mixture was filtered and the filtrate was concentrated. Flash chromatography (0.75% to 2% $CH_3OH/CH_2Cl_2$, silica gel) of the filtrate gave 0.16 g of the desired material as a light brown oil. MS(ES+) m/z 283.2 (M+H$^+$).

Example 84

Preparation of 4-Thiophen-3-yl-1-[3-(3-trifluoromethyl-phenyl)-propyl]-1H-imidazole a) Methanesulfonic Acid 3-(3-Trifluoromethyl-phenyl)-propyl Ester In a manner analogous to the preparation of Example 83(a), 3-(3-trifluoromethyl-phenyl)-propan-1-ol (0.94 g, 4.61 mmol), Et$_3$N (1.28 mL, 9.22 mmol) and MsCl (0.44 mL, 5.53 mmol) gave the desired compound as a light brown oil. $^1$H NMR (300 MHz, CDCl$_3$) δ 2.10–2.16 (m, 2H), 2.82–2.86 (t, 2H) 3.02 (s, 3H), 4.24–4.28 (t, 2H), 7.38–7.52 (m, 4H).

b) 4-Thiophen-3-yl-1-[3-(3-trifluoromethyl-phenyl)-propyl]-1H-imidazole

In a manner analogous to preparation of Example 83(b), the compound of Preparation 7 (0.32 g, 2.10 mmol). NaH (0.17 g, 60% dispersion in mineral oil, 4.20 mmol) and the compound of Example 84(a) (0.71 g, 2.52 mmol) gave 60 mg of the desired material as a light brown oil. MS(ES+) m/z 337.0 (M+H$^+$). Anal. ($C_{17}H_{15}N_2SF_3.0.55H_2O$) calcd: C, 58.97: H, 4.69; N, 8.09. found: C, 59.36; H, 4.53; N, 7.67.

Example 85

Preparation of 1-Biphenyl-2-ylmethyl-4-thiophen-3-yl-1H-imidazole

In a manner analogous to Example 81, the compound of Preparation 7 (0.20 g, 1.33 mmol), $K_2CO_3$ (0.37 g, 2.67 mmol) and 2-phenylbenzylbromide (0.35 g, 1.3 mmol) gave 53 mg of the desired material as a beige solid. MS(ES+) m/z 317.0 (M+H$^+$). Anal. ($C_{20}H_{16}N_2S.1.5TFA.1.0H_2O$) calcd: C, 54.65; H, 3.89 N, 5.54. found: C, 54.67; H, 3.569 N, 5.76.

Example 86

Preparation of 1-(4-Phenoxy-benzyl)-4-thiophen-3-yl-1H-imidazole

In a manner analogous to Example 81, the compound of Preparation 7 (0.23 g, 1.53 mmol), $K_2CO_3$ (0.42 g, 3.04 mmol) and p-phenoxybenzylbromide (0.42 g, 1.53 mmol) gave 0.13 g of the desired material as a beige solid. MS(ES+) m/z 333.2 (M+H$^+$). Anal. ($C_{20}H_{16}N_2SO.0.75H_2O$) calcd: C, 69.44; H, 5.10; N, 8.10. found: C, 69.61; H, 4.90; N, 7.90.

Example 87

Preparation of 1-(4-Isopropyl-benzyl)-4-thiophen-3-yl-1H-imidazole

In a manner analogous to Example 81, the compound of Preparation 7 (0.24 g, 1.57 mmol), $K_2CO_3$ (0.43 g, 3.11 mmol) and 4-isopropylbenzyl chloride (0.28 g, 1.57 mmol) gave 0.08 g of the desired material as a beige solid. MS(ES+) m/z 283.2 (M+H$^+$). Anal. ($C_{17}H_{18}N_2S$) calcd: C, 72.30; H, 6.42; N, 9.92. found: C, 72.00; H, 6.51; N, 9.76.

Example 88

Preparation of 1-[3-(3-Methoxy-phenyl)-propyl]-4-thiophen-3-yl-1H-imidazole a) Methanesulfonic Acid 3-(3-Methoxy-phenyl)-propyl Ester In a manner analogous to the preparation of Example 83(a), 3-(3-methoxy-phenyl)-propan-1-ol (0.83 g, 5.00 mmol). $Et_3N$ (1.40 mL, 10.0 mmol) and MsCl (0.46 mL, 6.00 mmol) gave the desired compound as a light brown oil. $^1$H NMR (300 MHz, CDCl$_3$) δ 2.04–2.09 (m, 2H), 2.69–2.74 (t, 2H) 2.99 (s, 3H), 3.82 (s, 3H), 4.22–4.26 (t, 2H), 6.70–6.80 (m, 3H), 7.16–7.19 (m, 1H).

b) 1-[3-(3-Ethoxy-phenyl)-propyl]-4-thiophen-3-yl-1H-imidazole

In a manner analogous to preparation of Example 83(b), the compound of Preparation 7 (0.23 g, 1.54 mmol), NaH (93 mg. 60% dispersion in mineral oil, 4.20 mmol) and the compound of Example 88(a) (0.40 g, 1.62 mmol) gave 0.18 g of the desired material as a light brown oil. MS(ES+) m/z 299.2 (M+H$^+$). Anal. ($C_{17}H_{18}N_2OS.0.25H_2O$) calcd: C, 67.41; H, 6.16; N, 9.25. found: C, 67.81; H, 6.16; N, 9.09.

Example 89

Preparation of 1-(4-Ethyl-benzyl)-4-thiophen-3-yl-1H-imidazole

In a manner analogous to Example 81, the compound of Preparation 7 (0.22 g, 1.47 mmol), $K_2CO_3$ (0.41 g, 2.97 mmol) and 4-ethylbenzyl chloride (0.24 g, 1.47 mmol) gave 53 mg of the desired material as a beige solid. MS(ES+) m/z 269.2 (M+H$^+$). Anal. ($C_{16}H_{16}N_2S.1.5TFA.0.25H_2O$) calcd: C, 51.41; H, 4.09; N, 6.31. found: C, 51.33; H, 3.91; N, 6.38.

Example 90

Preparation of 4-(4-Cyclohexyl-phenyl)-2-(3,4-dichloro-benzyl)-1H-imidazole

In a manner analogous to Example 48 (b), the compound of Example 49 (a) (0.53 g, 2.63 mmol) and 2-bromo-1-(4-cyclohexylphenyl)ethanone (0.30g, 1.10 mmol) gave 9.8 mg of the desired material after preparative reverse phase HPLC (10% to 90% $CH_3CN/H_2O$+0.1% TFA over 15 min.). MS (ES+) m/z 385.2 (M+H$^+$).

Example 91

Preparation of 1-((R)-1-Phenyl-ethyl)-4-thiophen-3-yl-1H-imidazole (R)-1-Phenyl-ethylamine (1.5 equivalents), glyoxylic acid (1.3 equivalents) and $K_2CO_3$ (2.5 equivalents) are combined in DMF. After 3h, add the 3-[1-isocyano-1-(toluene-4-sulfonyl)-methyl]-thiophene (1 equivalent) and stir the reaction at RT for 18 h. Pour the reaction mixture into brine and extract with $Et_2O$. Dry the combined organic extracts over $K_2CO_3$ and isolate the desired product by flash chromatography.

Example 92

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 ML of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 93

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 94

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A method for inhibiting Fab I which comprises administering to a subject in need thereof a compound which is:

1-Benzyl-4-(2-thienyl)-1H-imidazole;

1-Benzyl-4-(3-thienyl)-1H-imidazole;

1-Benzyl-4-(4-methoxyphenyl)-1H-imidazole;

1-(4-Methylbenzyl)-4-(3-thienyl)-1H-imidazole;

4-(4-Methoxyphenyl)-1-(4-methylbenzyl)-1H-imidazole;

1-(4-Chlorobenzyl)-4-(2-thienyl)-1H-imidazole;

1-(4-Chlorobenzyl)-4-(3-thienyl)-1H-imidazole;

1-(4-Chlorobenzyl)-4-(4-methoxyphenyl)-1H-imidazole;

1-(3,4-Dichlorobenzyl)-4-(2-thienyl)-1H-imidazole;

1-(3,4-Dichlorobenzyl)-4-[4-(trifluoromethyl)phenyl]-1H-imidazole;

1-(3,4-Dichlorobenzyl)-4-phenyl-1H-imidazole;

1-(4-Methoxybenzyl)-4-(3-thienyl)-1H-imidazole;

1-(4-Methoxybenzyl)-4-(4-methoxyphenyl)-1H-imidazole;

1-Benzo[1,3]dioxol-5-ylmethyl-4-thiophen-3-yl-1H-imidazole;

4-(2-Methoxy-phenyl)-1-naphthalen-2-ylmethyl-1H-imidazole;

1-(2,4-Dichloro-benzyl)-4-thiophen-3-yl-1H-imidazole;

4-Thiophen-3-yl-1-(3-m-tolyl-propyl)-1H-imidazole;

1-[3-(4-Methoxy-phenyl)-propyl]-4-thiophen-3-yl-1H-imidazole;

4-Thiophen-3-yl-1-[3-(3-trifluoromethyl-phenyl)-propyl]-1H-imidazole;

1-(4-Isopropyl-benzyl)-4-thiophen-3-yl-1H-imidazole;

1-[3-(3-Methoxy-phenyl)-propyl]-4-thiophen-3-yl-1H-imidazole;

1-(4-Ethyl-benzyl)-4-thiophen-3-yl-1H-imidazole;

1-(4-Methylbenzyl)-4-phenyl-1H-imidazole; or 1-(4-Methylbenzyl)-4-(2-thienyl)-1H-imidazole;

or a pharmaceutically acceptable salt thereof.

\* \* \* \* \*